US 6,741,344 B1

(12) United States Patent
Stern et al.

(10) Patent No.: US 6,741,344 B1
(45) Date of Patent: May 25, 2004

(54) METHOD AND APPARATUS FOR DETECTION OF FLUORESCENTLY LABELED MATERIALS

(75) Inventors: David Stern, Mt. View, CA (US); Peter Fiekowsky, Los Altos, CA (US)

(73) Assignee: Affymetrix, Inc., Santa Clara, CA (US)

( * ) Notice: Subject to any disclaimer, the term of this patent is extended or adjusted under 35 U.S.C. 154(b) by 387 days.

(21) Appl. No.: 09/699,852

(22) Filed: Oct. 30, 2000

Related U.S. Application Data

(63) Continuation of application No. 08/823,824, filed on Mar. 25, 1997, now Pat. No. 6,141,096, which is a continuation of application No. 08/195,889, filed on Feb. 10, 1994, now Pat. No. 5,631,734.

(51) Int. Cl.[7] ............................................. G01N 21/64
(52) U.S. Cl. .................... 356/317; 250/458.1; 356/417; 356/318
(58) Field of Search ................. 356/317, 318, 356/417; 250/458.1, 459.1, 461.1, 461.2; 436/518; 435/5

(56) References Cited

U.S. PATENT DOCUMENTS

| 3,216,313 A | 11/1965 | Chisholm |
| 3,385,160 A | 5/1968 | Dawson et al. |

(List continued on next page.)

FOREIGN PATENT DOCUMENTS

| WO | WO 8401031 | 3/1984 |
| WO | WO 90/15070 | 12/1990 |
| WO | WO 92/10092 | 6/1992 |
| WO | WO92/10092 | 6/1992 |
| WO | WO 93/09668 | 5/1993 |
| WO | WO 95/11995 | 5/1995 |

OTHER PUBLICATIONS

Alexay et al., "Fluorescence scanner employing a Macro Scannign Objective," Progress in Biomedical Optics, SPIE, Proceedings of fluorescence Detection IV, vol. 2705, pp. 63–72 (1996).

Benschop et al., "Confocal compact scanning optical microscope based on compact disk technology." *Chem. Abs.* 114(26):1179–1184, abstract No. 256643p.(Jul. 1, 1991).

Chee et al., "Accessing Genetic Informatin with High–Density DNA Arrays," *Science*, vol. 274; pp. 610–614 (Oct. 25, 1996).

(List continued on next page.)

*Primary Examiner*—F. L. Evans
(74) *Attorney, Agent, or Firm*—Philip L. MaGarrigle; Alan B. Sherr; Ivan D. Zitkovsky

(57) ABSTRACT

Fluorescently marked targets bind to a substrate 230 synthesized with polymer sequences at known locations. The targets are detected by exposing selected regions of the substrate 230 to light from a light source 100 and detecting the photons from the light fluoresced therefrom, and repeating the steps of exposure and detection until the substrate 230 is completely examined. The resulting data can be used to determine binding affinity of the targets to specific polymer sequences.

22 Claims, 12 Drawing Sheets

U.S. PATENT DOCUMENTS

| | | |
|---|---|---|
| 3,632,212 A | 1/1972 | Bernal |
| 3,798,449 A | 3/1974 | Reinheimer et al. |
| 3,802,966 A | 4/1974 | Delekto et al. |
| 3,984,171 A | 10/1976 | Hotchkiss |
| 4,016,855 A | 4/1977 | Mimata |
| 4,070,111 A | 1/1978 | Harrick |
| 4,176,925 A | 12/1979 | Kocher et al. |
| 4,180,739 A | 12/1979 | Abu-Shumays |
| 4,204,929 A | 5/1980 | Bier |
| 4,342,905 A | 8/1982 | Fujii et al. |
| 4,417,260 A | 11/1983 | Kawai et al. |
| 4,448,534 A | 5/1984 | Wertz et al. |
| 4,537,861 A | 8/1985 | Elings et al. |
| 4,579,430 A | 4/1986 | Bille |
| 4,580,895 A | 4/1986 | Patel |
| 4,626,684 A | 12/1986 | Landa |
| 4,708,494 A | 11/1987 | Kleinerman |
| 4,772,125 A | 9/1988 | Yoshimura et al. |
| 4,786,170 A | 11/1988 | Groebler |
| 4,810,869 A | 3/1989 | Yabe et al. |
| 4,844,617 A | 7/1989 | Keldermann et al. |
| 4,878,971 A | 11/1989 | Tsunekawa et al. |
| 4,963,498 A | 10/1990 | Hillman et al. |
| 5,061,075 A | 10/1991 | Alfano et al. |
| 5,132,524 A | 7/1992 | Singh et al. |
| 5,143,854 A | 9/1992 | Pirrung et al. |
| 5,188,963 A | 2/1993 | Stapleton |
| 5,192,980 A | 3/1993 | Dixon et al. |
| 5,198,871 A | 3/1993 | Hill, Jr. et al. |
| 5,200,051 A | 4/1993 | Cozzette et al. |
| 5,214,531 A | 5/1993 | Torii et al. |
| 5,235,180 A | 8/1993 | Montagu |
| 5,281,516 A | 1/1994 | Stapleton et al. |
| 5,300,779 A | 4/1994 | Hillman et al. |
| 5,304,487 A | 4/1994 | Wilding et al. |
| 5,304,810 A | 4/1994 | Amos |
| 5,310,469 A | 5/1994 | Cunningham et al. |
| 5,320,808 A | 6/1994 | Holen et al. |
| 5,346,672 A | 9/1994 | Stapleton et al. |
| 5,381,224 A | 1/1995 | Dixon et al. |
| 5,382,511 A | 1/1995 | Stapleton |
| 5,384,261 A | 1/1995 | Winkler et al. |
| 5,405,783 A | 4/1995 | Pirrung et al. |
| 5,424,186 A | 6/1995 | Fodor et al. |
| 5,424,841 A | 6/1995 | Van Gelder et al. |
| 5,436,129 A | 7/1995 | Stapleton |
| 5,451,500 A | 9/1995 | Stapleton |
| 5,459,325 A | 10/1995 | Hueton et al. |
| 5,474,796 A | 12/1995 | Brennan |
| 5,486,335 A | 1/1996 | Wilding et al. |
| 5,494,124 A | 2/1996 | Dove et al. |
| 5,498,392 A | 3/1996 | Wilding et al. |
| 5,527,681 A | 6/1996 | Holmes |
| 5,532,873 A | 7/1996 | Dixon |
| 5,571,639 A | 11/1996 | Hubbell et al. |
| 5,572,598 A | 11/1996 | Wihl et al. |
| 5,578,832 A | 11/1996 | Trulson et al. |
| 5,583,342 A | 12/1996 | Ichie |
| 5,585,639 A | 12/1996 | Dorsel et al. |
| 5,631,734 A | 5/1997 | Stern et al. |
| 5,646,411 A | 7/1997 | Kain et al. |
| 5,672,880 A | 9/1997 | Kain |
| 5,737,121 A | 4/1998 | Dixon et al. |
| 5,760,951 A | 6/1998 | Dixon et al. |
| 5,861,242 A | 1/1999 | Chee et al. |
| 5,981,956 A | 11/1999 | Stern |
| 6,141,096 A * | 10/2000 | Stern et al. ............ 356/318 |

OTHER PUBLICATIONS

Dixon et al., "Confocal scanning beam laser microscope/macroscope: Applications in Fluorescence," Progress in Biomedical Optics, SPIE, Proceedings of Flrorescence Detection IV, vol. 2703, pp. 44–52 (1996).

Ekins et al., "Development of microspot multianalyte ratiometric immunoassay using dual fluorescent–labelled antibodies," *Analytica Chimica* ACTA 227:73–96. (Dec. 1, 1989).

Ekins et al. Multianalyte microspot immunoassay–microanalytical 'compact disk of the future, *Clin Chem* 37(11):1955–1967, (Nov. 1991).

Fodor et al., "Light–Directed, Spatially Addressable Parallel Chemical ASynthesis," *Science*, vol. 251, pp. 767–773 (Feb. 15, 1991).

Lockhart et al., "Expression monitoring by hybridization to high–density oligonucleotide arrays," *Nature Biotechnology*, vol. 14, No. 13, pp. 1675–1680 (Dec. 1996).

Pease et al., "Light–generated oligonucleotide arrays for rapid DNA sequence analysis," *Proc. Natl. Acad. Sci. USA*. vol. 91, pp. 5022–5026 (May 1994).

Quesada et al., "High–sensitivity DNA detection with a laser–excited confocal fluorescent gel scanner." *Biotechniques* 10:616–625. (1991).

Sapolsky et al., "Mapping Genomic Library Clones Using Oligonucleotide Arrays," *Genomics*, vol. 33, Article No. 0219, pp. 445–456 (1996).

van der Voort et al., "Design and use of a computer controlled confocal microscope for biological applications." *Scanning* 7:68–78. (1985).

White et al., "An evaluation of confocal versus conventional imaging of biological structures by fluorescent light microcopy." *J. Cell Biol.* 105:41–48. (Jul. 1987).

Yamamoto et al., "Features and applications of the laser scanning microscope," *J. Mod. Optics* 37:1691–1701, (1990).

Yamanoto et al., "Features and applications of the laser scannign microscope," *Journal of Modern Optics*, vol. 37, No. 11, pp. 1691–1701 (1990).

* cited by examiner

\* Counter 1 is enabled to count;
Data from Counter 2 is read and stored

\*\* Counter 2 is enabled to count;
Data from Counter 1 is read and stored

METHOD AND APPARATUS FOR DETECTION OF FLUORESCENTLY LABELED MATERIALS

This is a continuation of application Ser. No. 08/823,824 filed Mar. 25, 1997 now U.S. Pat. No. 6,141,096, which is a continuation of Ser. No. 08/195,889 filed Feb. 10, 1994, now U.S. Pat. No. 5,631,134 the disclosures of which are incorporated by reference.

GOVERNMENT RIGHTS NOTICE

This invention was made with Government support under grant nos. DE-FG03-92ER81275 (SBIR) awarded by Department of Energy and/or H600813-1, -2 between Affymetrix, Inc. and the National Institute of Health. The Government has certain rights in this invention.

BACKGROUND OF THE INVENTION

The invention provides a method and associated apparatus for detecting and analyzing reactions of fluorescently marked materials on a single substrate surface.

Certain macromolecules are known to interact and bind to other molecules having a very specific three-dimensional spatial and electronic distribution. Any large molecule having such specificity can be considered a target. The various molecules that targets selectively bind to are known as probes.

Methods and devices for detecting fluorescently marked targets on devices are known. Generally, the devices includes a microscope and a monochromatic or polychromatic light source for directing light at a substrate. A photon counter detects fluorescence from the substrate, while an x-y translation stage varies the location of the substrate. A computer controls the movement of the x-y translation table and data collection. Such devices are discussed in, for example, U.S. Pat No. 5,143,854 (Pirrung et al.) incorporated herein by reference for all purposes. See also PCT WO 92/10092 also incorporated herein by reference for all purposes.

Light from the light source is focused at the substrate surface by manually adjusting the microscope. Manual adjustment is, on occasion, time consuming and inconvenient. Moreover, due to inherent imperfections present in the x-y translation table and substrate, there is a possibility that the substrate will be out of focus as it is moved from one region to another. As a result, the data collected may be misrepresented.

Also, temperature sometimes impact a chemical reaction between targets and probes. Generally, targets are more active or form stronger bonds at lower temperatures while the converse is true at higher temperatures. However, if the temperature is too low, the binding affinity of the target may become excessively strong, thus causing target to bind with complements (matches) as well as non-compliments (mismatches). Hence, the ability to control temperature may affect optimum binding between the targets and probes while minimizing mismatches.

In addition, the microscope detection devices are uneconomical to use. Typically, these devices incorporates the use of a microscope, and a multichannel scaler, both of which are costly.

From the above, it is apparent that an improved method and apparatus for detecting fluorescently labeled targets on a substrate is desired.

SUMMARY OF THE INVENTION

Methods and devices for the detection of fluorescently labeled targets on a substrate are disclosed. The detection method and devices utilize a substrate having a large variety of probes at known locations on its surface. The substrate, when placed in a confocal detection device, is exposed to fluorescently labeled targets that bind to one or more of the probes.

The confocal detection device includes a monochromatic or polychromatic light source, means for directing an excitation light from the light source at the substrate, means for focusing the light on the substrate, means for controlling temperature of the substrate during a reaction, means for detecting fluorescence emitted by the targets in response to the excitation light by directing the fluorescence through confocal pinholes, and means for identifying the region where the fluorescence originated. The means for controlling the temperature may include a temperature controlled fluid filled flow cell. The means for detecting the fluorescent emissions from the substrate, in some embodiments, include a photomultiplier tube. The means for focusing the excitation light to a point on the substrate and determining the region the fluorescence originated from may include an x-y-z translation table. Further, translation of the x-y-z table, temperature control and data collection are recorded and managed by an appropriately programmed digital computer.

In connection with one aspect of the invention, methods for analyzing the data collected by the fluorescent detection methods and devices are disclosed. Data analysis includes the steps of determining fluorescent intensity as a function of substrate position from the data collected; removing "outliers" (data deviating from a predetermined statistical distribution); and calculating the relative binding affinity of the targets from the remaining data. The resulting data are displayed as an image with the intensity in each region varying according to the binding affinity between targets and probes therein.

By using confocal optics, as well as focusing and temperature regulating techniques in conjunction with the data analysis methods, it is possible to quickly and accurately determine the relationship between structure and activity of certain molecules. Therefore, the potential for discovering novel probes with desirable pattern of specificity for biologically important targets is dramatically increased.

A further understanding of the nature and advantages of the inventions herein may be realized by reference to the remaining portions of the specification and the attached drawings.

DESCRIPTION OF THE PREFERRED EMBODIMENT

Contents

I. Definitions

II. Details of One Embodiment of a Fluorescent Detection Device

III. Details of the Operation of a Fluorescent Detection Device

IV. Details of One Embodiment of Data Analysis to Determine Relative Binding Strength of Targets V. Conclusion

I. Definitions

The following terms are intended to have the following general meanings as they are used herein:
1. Complementary: Refers to the topological compatibility or matching together of interacting surfaces of a probe molecule and its target. Thus, the target and its probe can be described as complementary, and furthermore, the contact surface characteristics are complementary to each other.
2. Probe: A probe is a molecule that is recognized by a particular target. Examples of probes that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.
3. Target: A target is a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

II. Fluorescent Detection Device

Figure 1A:
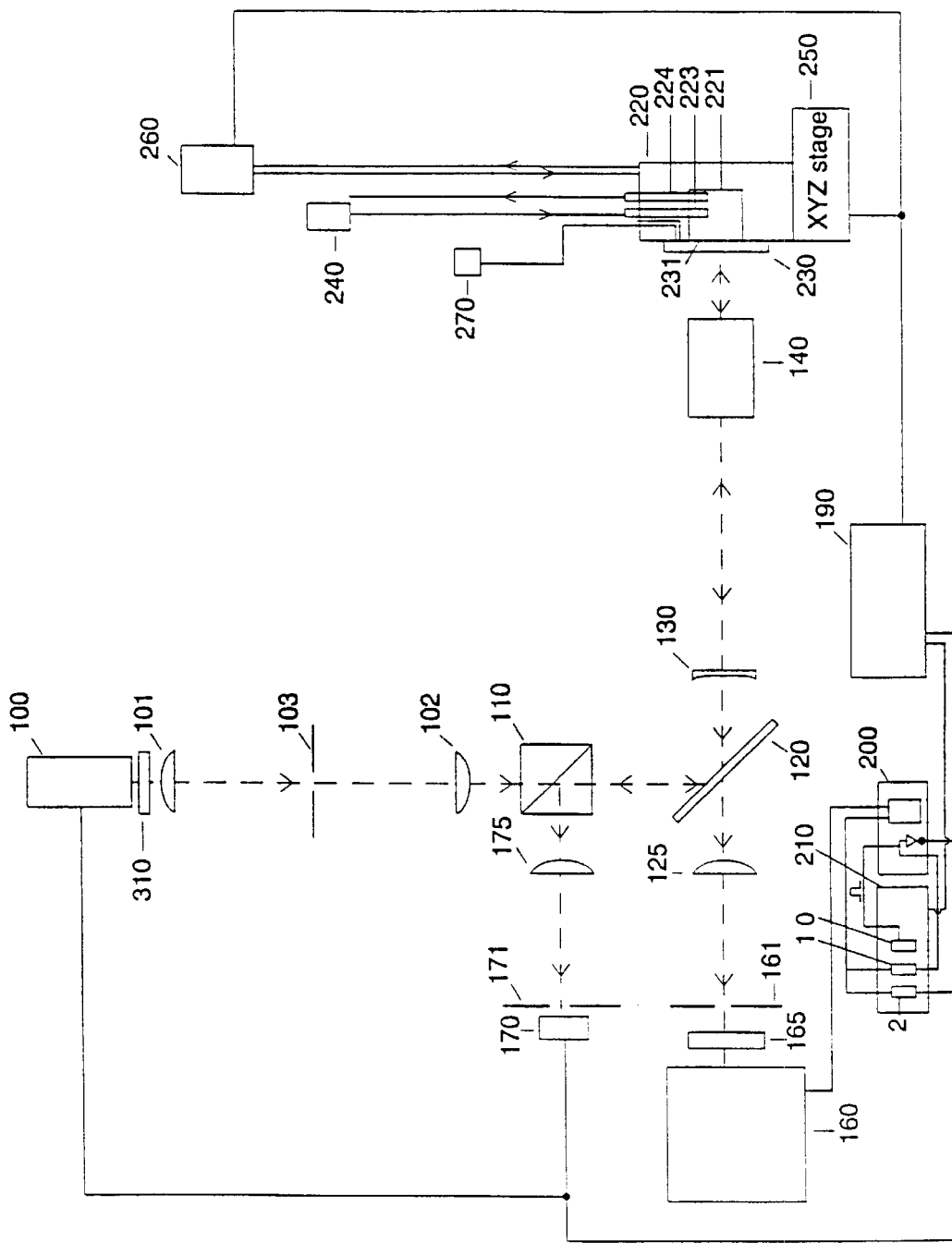
FIG. 1a shows a detection system for locating fluorescent markers on the substrate.

FIG. 1a schematically illustrates a device used to detect fluorescently labeled targets on a substrate. Substrate 230 comprises a number of presynthesized probes on its surface 231. Such probes may be synthesized according to techniques described in U.S. Pat. No. 5,143,854 or PCT WO 92/10092 or other techniques.

Substrate 230 is preferably transparent to a wide spectrum of light. In some embodiments, substrate 230 is made of a conventional microscope glass slide or cover slip. It is preferable that the substrate be as thin as possible while still providing adequate physical support. Preferably, the substrate is less than about 1 mm thick, more preferably less than 0.5 mm thick. Typically, the substrate is a microscope glass slide of about 0.7 mm or 700 $\mu$m thick. In alternative embodiments, the substrate may be made of quartz or silica.

Substrate 230 is mounted on a flow cell 220. Flow cell 220 is a body having a cavity 221 on a surface thereof. The cavity is between about 50 and 1500 $\mu$m deep with a preferred depth of 1000 $\mu$m. The bottom of the cavity is preferably light absorbing so as to prevent reflection of impinging light. In addition, the flow cell may be impervious to light.

When mounted to the flow cell, the substrate seals the cavity except for inlet port 223 and outlet port 224. According to a specific embodiment, the substrate is mounted to the flow cell by vacuum pressure generated from a vacuum pump 270. Optionally, one or more gaskets may be placed between the flow cell and substrate and the intervening space is held at vacuum to ensure mating of the substrate to the gaskets.

Reagents, such as fluorescein labeled targets (fluorescence peak at about 530 nm) are injected into the cavity 221 through the inlet port 223 by a pump 240 or by using a syringe. The pump may be, for example, a Masterflex peristaltic pump made by Cole-Parmer Instrument Co or equivalent. Within the cavity, the reagents bind with one or more complementary probes on surface 230 of the substrate. The reagents are circulated into the cavity via inlet port 221 by and exit through the outlet port 224 for recirculation or disposal.

Flow cell 220 permits the substrate to remain in constant contact with reagents during detection, thereby allowing the substrate to be in equilibrium with targets therein. This arrangement also permits the user to manipulate test conditions without dismounting the substrate. In some embodiments, the flow cell provides means for controlling the temperature within the flow cell. The means for controlling temperature may be a recirculating bath device 260 that flows water through channels formed in the flow cell. In the specific embodiment, device 260 is a refrigerated circulating bath with a RS232 interface, catalog number 13270-615 distributed by VWR or equivalent. However, means such as a circulating air device, a resistance heater, a peltier device (thermoelectric cooler) or others may also be employed. Computer 190 monitors and controls device 260, thereby maintaining the flow cell at a desired temperature. Computer 190 may be selected from a wide variety of computers including, for example, a Gateway 486DX computer or a similar appropriately programmed computer.

Controlling the temperature in the flow cell is advantageous because temperature affects the chemical reaction between targets and probes. For example, the bond between the targets and probes is generally stronger at lower temperatures. However, if the temperature is too low, the binding affinity between targets and probes may become excessively strong so as to produce apparent (but erroneous) matches. Thus, temperature can be controlled to maximize the binding affinity of complementary targets while minimizing mismatches.

Flow cell 220 is mounted on a x-y-z translation table 230. X represents the horizontal direction; y represents the vertical direction; and z represents the direction into and away from the microscope objective such that focusing may be performed. In some embodiments, the x-y-z translation table may be a Pacific Precision Laboratories Model ST-SL06R-B5M. Movement of the translation table is controlled by computer 190.

A light source 100 generates a beam of light to excite the fluorescein labeled targets in the flow cell. The light source may be a argon laser that generates a beam having a wavelength of about 488 nm, which in some embodiments may be a model 2017 or model 161C manufactured by Spectra-Physics. Other lasers, such as diode lasers, helium lasers, dye lasers, titanium sapphire lasers, Nd:YAG lasers or others may also be employed. The laser is directed at surface 230 through an optical train comprised of various optical elements which will be described below in detail.

The beam generated by laser 100 is typically nearly collimated and nearly Gaussian. However, a spatial filter may be optionally located in front of laser 100 to improve the Gaussian profile of the beam. The spatial filter may comprise of a lens 101, a confocal pinhole 103 and a lens 102. Lens 101 and 102, for example, may be ½" diameter 50 mm focal length anti-reflection coated plano convex glass lens or equivalent. Both lenses are configured such that both their back focal planes coincide with confocal pinhole 103. Pinhole 103, for example, may have a aperture of 30 µm.

Thereafter, the light passes through a beam splitter 110 to a dichroic mirror 120. The beam splitter may be, for example, a non-polarizing 50% beam splitter cube made by Melles Griot model number 03BSC007 or equivalent while the dichroic mirror may be a LWP-45° S-488R/520T-1025 made by CVI Laser Corp. or equivalent. The functions of the beam splitter cube will later be described in more detail.

In some embodiments, dichroic- mirror 120 passes light having a wavelength greater than about 520 nm, but reflects light having a wavelength of about 488 nm. Consequently, the 488 nm light from the laser is reflected by dichroic mirror 120 toward optical lens 130. Optical lens 130, in the specific embodiment, is ½' diameter –50 mm focal length anti-reflection coated plano-concave glass lens made by Newport or equivalent. The light then passes through a microscope objective 140 to substrate 230 for magnification of the image sample. Microscope objective 140, in some embodiments, may be a 10× 0.3 NA microscope objective, but other magnifications could also be used. In a preferred embodiment, the distance between lens 130 and microscope objective 140 is about 100 mm.

Microscope objective 140 focuses the light on surface 231, thereby exciting the fluorescein labeled targets. Preferably, the microscope objective produces a spot about 2 µm in diameter in its focal plane. The optical train described in the above embodiments produces a 2 µm diameter focal spot when used with a laser which generates a beam diameter of 1.4 mm, such as the Spectra-Physics model 2017.

In alternative embodiments, the 2 µm spot may be easily obtained when other types of light sources with different beam diameters are used. Since the diameter of the focal spot is inversely proportional to the diameter of the collimated beam produced by lens 102 the desired spot size may be achieved by varying the focal lengths of the spatial filter. Alternatively, a beam expander may be used to expand or compress the beam from the light source to obtain the desired spot size. For example, if a model 161C which generates a beam diameter of 0.7 mm, a 2 µm diameter focal spot may be achieved if the ratio of the lens in the spatial filter is 1:2 instead of 1:1. Thus, by varying the focal lengths of the lenses in the spatial filter and/or using a beam expander, the appropriate excitation spot size may be achieved from various beam diameters.

In a preferred embodiment, the 2 µm spot has a power of 50 µW. Depending on the light source used, a variable neutral density filter 310 may be inserted between the laser 100 and the optical train to attenuate the power of the laser to the desired power level.

In response to the excitation light, fluorescein labeled targets in the flow cell fluoresce light having a wavelength greater than about 520 nm. The fluorescence will be collected by the microscope objective 140 and passed to optical lens 130. Optical lens 130 collimates the fluorescence and passes it to dichroic mirror 120. In practice, light collected by microscope objective contains both fluorescence emitted by the fluorescein and 488 nm laser light reflected from the surface 231.

The laser component reflected from the substrate is reflected by dichroic mirror 120 back to beam splitter 110 Beam splitter 110 directs the laser component through a lens 175. The lens, in some embodiments, may be a ½" diameter 50 mm focal length anti-reflection coated plano convex glass lens made by Newport, but equivalent thereof may be used. Lens 175 focuses the laser component to a photodiode 170. Preferably, a confocal pinhole 171 is located between lens 175 and photodiode 170. Confocal pinhole transmits substantially only the reflected light originating from the focal plane of the microscope to photodiode 170 while reflected light originating from out-of-focus planes are blocked. In some embodiments confocal pinhole 171 has an aperture of 50 µm. Photodiode 170 generates a voltage corresponding to the intensity of the detected light. Photodiode may be, for example, a 13 DSI007 made by Melles Griot or equivalent, or other light detection devices, such as photomultiplier tube or avalanche photodiode may be used. Output from the detection device is used by computer 190 to focus the laser at a point on surface 230 of substrate 230.

As for the fluorescent component, most of it will pass through the dichroic mirror 120 since its wavelength is greater than about 520 nm. The fluoresced light is then focused by a lens 125 to a photomultiplier tube 160 for detecting the number of photons present therein. Lens 125, in a preferred embodiment, is a ½" diameter 50 mm focal length anti-reflection coated plano convex glass lens made by Newport, but equivalent lens may be used. A confocal pinhole 161 may be located adjacent to lens 125. Confocal pinhole transmits florescence originating from the focal plane and filters out light originating from other planes, such as from the glass or reagent. Accordingly, the signal-to-noise ratio of the fluoresced light is increased. Additionally, a filter 165 is preferably located between photomultiplier tube and confocal pinhole 161. In a specific embodiment, the filter transmits light having a wavelength greater than about 515 nm such as an Omega Optical 515 EFLP. In an alternative embodiment, the filter may transmit light having a wavelength between about 515 and 545 nm such as a 530 DF30 made by Omega Optical. Thus, photomultiplier tube 160 detects substantially only fluoresced light.

In the specific embodiment, photomultiplier tube 160 is a Hamamatsu R4457P photomultiplier tube with Hamamatsu C3866 preamplifier/discriminator. The Photomultiplier tube generates approximately a 2 mV pulse for each photon detected. Each of these 2 mV pulses are converted to a TTL pulse by the preamplifier/discriminator. The TTL pulses, each one corresponding to a photon detected by the photomultiplier tube, are then collected by a data acquisition board 210. The data acquisition board may be a National Instruments "Lab-PC+" or equivalent.

Data acquisition board 210, typically, contains an Intel 8254 or equivalent counter/timer chip. This chip contains three counters, counter 0, counter 1 and counter 2. Counter 0 controls the operations of counters 1 and 2 for collecting data. Preferably, counter 0 is programmed to generate a square wave with a period which is equal to twice the data acquisition time per pixel. The output of counter 0 is coupled to an external circuit board 200 which provides logic for inverting the square wave. In a preferred embodiment, the inverted output of counter 0 is connected to the gate input of counter 2 while the non-inverted output is connected to the gate input of counter 1.

In a preferred embodiment, the data acquisition board is not be able to read or store the fast 10 ns pulses generated by preamplifier/discriminator (it is too fast for the 8254 chip). To solve this problem, external circuit board 200 may additionally provide means for slowing down the pulses. For example, the logic in external circuit board 200 may convert these pulses to 50 ns pulses with at least a 50 ns interval between pulses.

The output of the C3866 preamplifier/discriminator, via external circuit board 200, is connected to the clock inputs of counters 1 and 2. When counter 1 or counter 2 is gated on, it counts pulses generated by the preamplifier/discriminator; when it is gated off, it ceases to count and computer 190 reads the accumulated number of counts therein. After the computer reads the count from either counter 1 or 2, it is initialized to zero. Counter 1 or 2 is initialized on the first clock pulse after the gate input goes high. The initialization pulse is about a 50 ns pulse that is generated by the logic in the external circuit board 200 about 50 ns after each transition of the square wave signal from counter 0. The data stored in counter 1 or 2 represents the photon count as a function of substrate position.

After data are collected from a region of the substrate, substrate 230 is moved so that light can be directed at a different region on the substrate. The process is repeated until all regions on the substrate have been scanned. Generally, regions that contain a complementary probe will tend to exhibit a higher photon count than regions that do not contain a complementary probe.

Although the above embodiments have been described for use in detecting emissions of fluorescein excited by an 488 nm argon laser, it will be apparent to those skill in art that other dyes and excitation sources may used by simply modifying the elements in the optical train. For example, dichroic mirror 120 may be changed accordingly to pass light having a wavelength comparable to the fluorescence peak of the dye used, but reflect light from the excitation source. Also, filter 165 is changed to pass substantially only light having a wavelength similar to the fluorescence peak of the dye used. In this manner, the detection device can be easily modified to accommodate other types of excitation light and/or dyes.

Figure 1B:
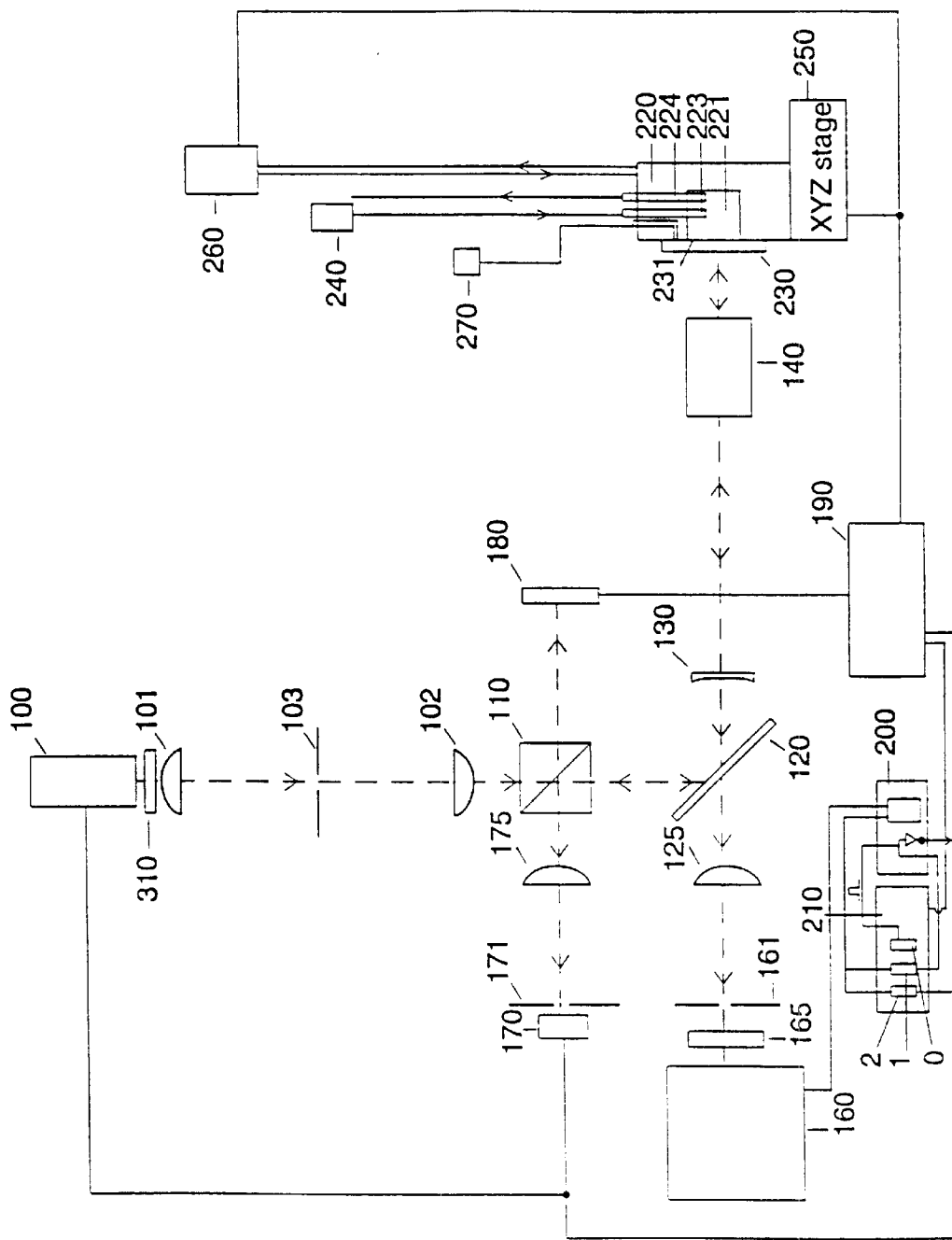
FIG. 1b shows an alternative embodiment of a detection system for locating fluorescent markers on the substrate.

FIG. 1*b* illustrates an alternative embodiment of the fluorescence detection device shown in FIG. 1*a*. FIG. 1*b* is similar to the one shown in FIG. 1*a* and the common elements have been numbered with the same reference numerals. The main difference between this embodiment and that of FIG. 1*a* is that a photodiode 180 is provided to detect a component of the light generated by laser 100. Light generated by the laser, as in FIG. 1*a*, is directed at the beam splitter. However, a component of this light is directed to photodiode 180. Photodiode 180 generates a voltage value representing the intensity of the light. This voltage signal is used by the computer 190 to monitor and control the intensity of the laser.

Figure 1C:
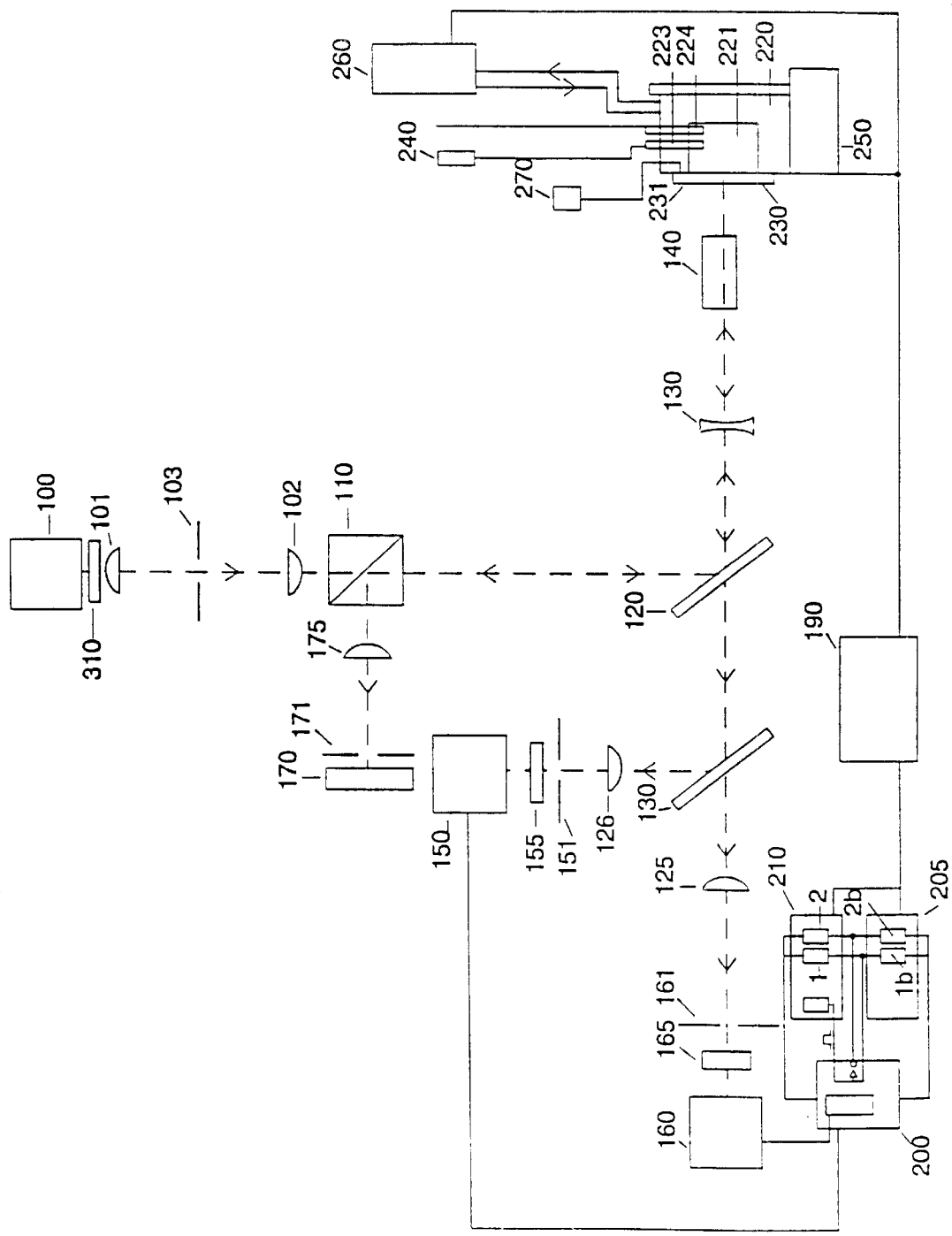
FIG. 1c shows another embodiment of a detection system for locating fluorescent markers on the substrate.

FIG. 1*c* illustrates an alternative embodiment of the fluorescence detection device. FIG. 1*c* is similar to the embodiment shown in FIG. 1*a* and the common elements have been numbered with the same reference numerals. However, the embodiment in FIG. 1*c* provides means for detecting a second fluorescent color. Two color detection is required when two different types of targets, each labeled with a different dye, are exposed to a substrate synthesized with probes. In some embodiments, fluorescein and rhodamine dyes may be used to label two different types of targets respectively. Typically, each dye will have a fluorescence peak at different wavelengths. For example, the fluorescence peak of fluorescein is about 530 nm while that of a typical rhodamine dye is about 580 nm.

To detect the second fluorescent color, a second dichroic mirror 300 is employed. If rhodamine and fluorescein were used, then dichroic mirror 300 is designed to pass light having a wavelength greater than about 570 nm (rhodamine emissions) and reflect light having a wavelength less than about 560 nm (fluorescein emissions). Light with a wavelength less than 560 nm is reflected to a lens 126 and through a confocal pinhole 151. Lens 126, may be equivalent to lens 125 while confocal pinhole 151 may be similar to confocal pinhole 161. Filter 155 then filters the less than 560 nm light before entering a second photomultiplier tube 150. Filter 155 may be an Omega Optical 530DF30 or equivalent that passes light with a wavelength between about 515–545 nm. This ensures that substantially only fluorescein emissions are detected by the photomultiplier 150.

On the other hand, light having a wavelength greater than 570 nm passes through dichroic mirror 300 to a lens 125. Lens 125 then directs the greater than 570 nm light through a pinhole 161 and a filter 165 before entering photomultiplier tube 160. Filter 165 may be a Schott OG570 or equivalent which passes light having a wavelength greater than 570 nm, thereby ensuring substantially only rhodamine emissions are detected by photomultiplier 160.

Output of the preamplifier/discriminator from the photomultiplier tube 150 is processed by the external circuit board 200 before being connected to counters 1*b* and 2*b* on the data acquisition board 205. Data collection by counters 1*b* and 2*b* are controlled by counter 0 from data acquisition board 210 which generates a square wave to the gated inputs of the counters 1 and 2 via the external circuit board 200, similar to that of counters 1 and 2 on data acquisition board 210.

According to the embodiment in FIG. 1*c*, two fluorescence color can be detected by employing a second dichroic mirror, photomultiplier tube and associated lens, confocal pinhole and filter. The embodiment illustrated in FIG. 1*c* may be expanded by one skill in the art to detect more than two fluorescence colors by employing an additional dichroic mirror, photomultiplier tube and associated lens, confocal pinhole and filter for each additional fluorescence color to be detected.

III. Details on the Operation of a Fluorescent Detection Device

In the specific embodiment, data are acquired continuously along a line which is broken up into data points or pixels. The pixel size preferably ranges from 1 to 100 $\mu$m. Since pixels are preferably square, the distance between scan lines will generally be between 1 to 100 $\mu$m. Each of these pixels will be used to form a digital image. The image resolution (i.e., the degree of discernable detail) depends upon the number of pixels that forms the image. The greater the number of pixels, the closer the digitized data will approximate the original image. Therefore, it is desirable to have as many pixels as possible. However, the number of pixels is directly related to the length of time required to scan the sample. In practice, it is found that having about 16 to 100 pixels per feature (or about 4–10 pixels along the length of the feature) is preferable to achieve the desire resolution in a reasonable amount of time.

The number of photons that is detected in each pixel is contingent upon several factors. The most obvious factor, of course, is the amount of fluorescently labeled targets present in the pixel. Other, but not so obvious, factors include the intensity of the excitation light, length of time that the targets are excited, and quantum efficiency of the photocathode at the fluorescence emission wavelength.

For example, exciting a region of about 2 $\mu$m with 50 $\mu$W of power will yield approximately 1600 W/cm$^2$ or 3.9×10$^{21}$ photons/(sec cm$^2$). At this intensity, the fluorescence rate is $Q_e k_a k_f/(k_a+k_f)=1.1×10^6$/sec (see Table I) with a photodestruction rate of $Q_b k_a k_f/(k_a+k_f)=36$/sec. In a typical substrate synthesized with polymer sequences at about 5 nm apart, approximately 4×10$^4$ molecules/$\mu$m$^2$ or 1.25×10$^5$ molecules will be present in the excitation volume. If it is estimated that about 1% of these sequences bind with fluorescein labeled targets, then about 1250 molecules are excited or 1.4×10$^9$ fluorescence photons are generated per second. However, in a typical detection device, only about 2% of these photons are collected by the microscope objective while about 98% never even make it into the optical train of the detection device. Of the 2% collected, about 50% are lost in the optical train and of the remaining photons, only about 10% are detected by the photomultiplier tube due to quantum efficiency of the photocathode at the fluorescein emission wavelength. Thus, approximately 1.4×10$^6$ photons might be counted per second. From the above, it is apparent that these factors affect the number of photons detected at each pixel.

TABLE I

Fluorescein Optical Parameters
[Tsien, R.Y., Waggoner, A. Fluorophores for confocal microscopy: photophysics and photochemistry. In Handbook of Biological Confocal Microscopy; Pawley, J., Ed.; Plenum Press: New York, 1990; pp. 169–178]

| | |
|---|---|
| Absorption cross section, $\sigma$, cm$^2$molecules$^{-1}$ | 3.06 × 10$^{-16}$ |
| Fluorescence rate constant, $k_f$, s$^{-1}$ | 2.2 × 10$^8$ |
| Absorption rate constant (1600 W/cm$^2$) $k_s$, s$^{-1}$ | 1.2 × 10$^6$ |
| Fluorescence quantum efficiency, $Q_e$ | 0.9 |
| Photodestruction efficiency, $Q_b$ | 3 × 10$^{-5}$ |

In the present invention, it is preferable to detect as many photons as possible, preferably about 1000 photons per pixel in pixels containing complementary probes and targets because the signal-to-noise ratio is equal to the square root of the number of photon counts. Since the number of photons collected will vary according to the power and length of time the targets are excited by the light, the signal-to-noise ratio may be improved by increasing the laser power or length of time the substrate is exposed to the laser or a combination thereof.

Figure 2:
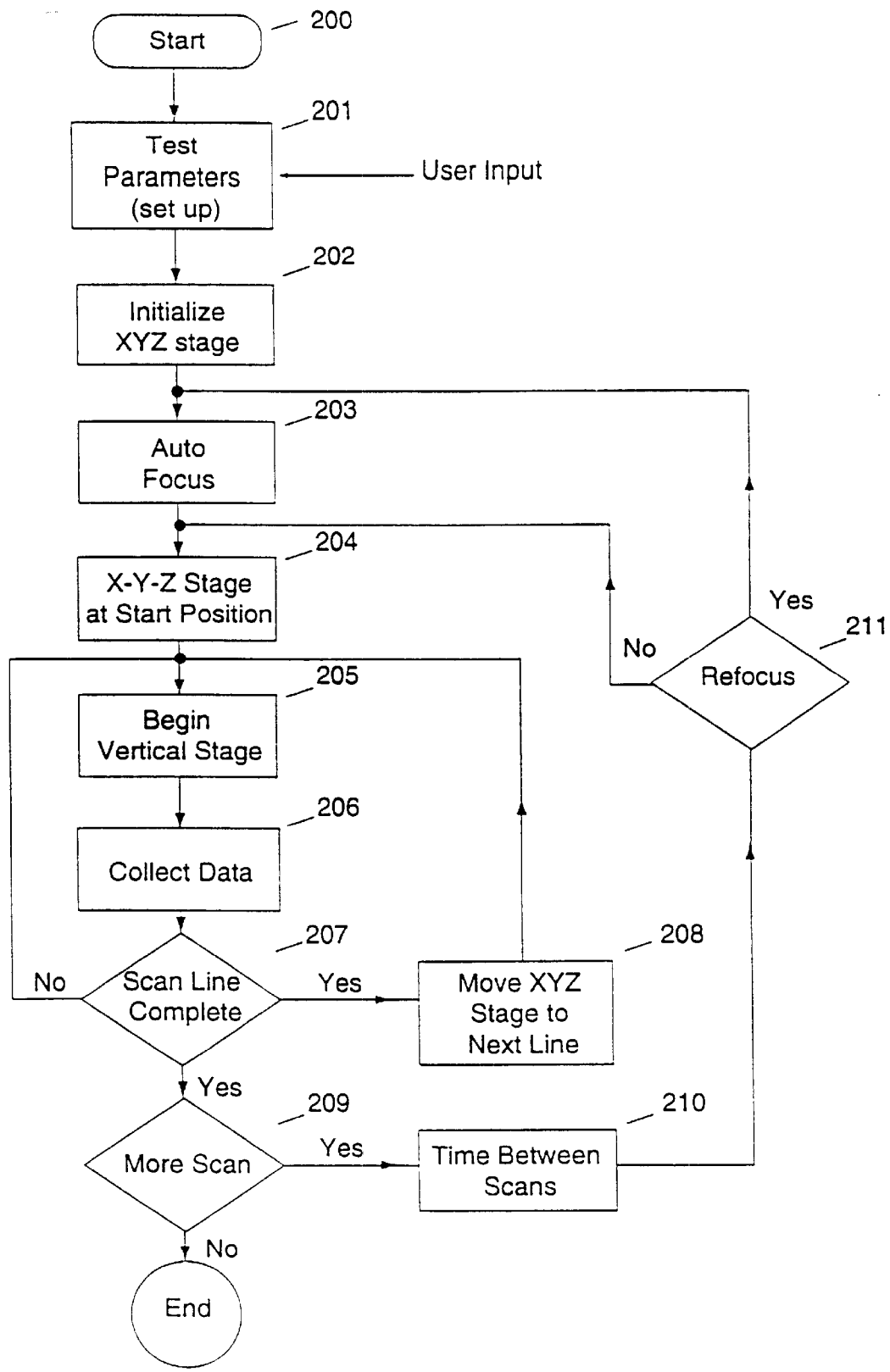
FIG. 2 is a flow chart illustrating the operation of the detection system.

FIGS. 2–6 are flow charts describing a specific embodiment. FIG. 2 is an overall description of the system's operation. Referring to FIG. 2, the detection system is initialized at step 200. At step 201, the system prompts the user for test parameters such as:
 a) temperature of the substrate;
 b) number of scans to be performed;
 c) time between scans;
 d) refocus between scans;
 e) pixel size;
 f) scan area; and
 g) scan speed.

The temperature parameter controls the temperature at which detection is performed. Temperature may vary depending on the type of polymers being tested. Preferably, testing is done at a temperature that produces maximum binding affinity while minimizing mismatches.

The number of scan parameter corresponds to the number of times the user wishes to scan the substrate while the time between scans parameter controls the amount of time to wait before commencing a subsequent scan. In this manner, the user may perform a series of scan and if desired, each at a different temperature. Preferably, the time between scans is chosen to allow the system to reach chemical equilibrium before commencing a subsequent scan.

In an alternative embodiment, means may be provided to increase the temperature at set increments automatically after each scan. Further, the user may optionally choose to refocus the substrate after each scan.

The pixel size parameter dictates the size of each data collection point. Generally, the size is chosen which results in at least 16 data collection points or pixels per synthesis region ("feature").

Scan area parameter corresponds to the size of the substrate to be tested. Scan speed parameter sets the length of time the laser excites each pixel. The slower the speed, the higher the excitation energy per pixel which will result in higher fluorescence count per pixel. Thus, increasing the laser power or decreasing the scan speed or a combination thereof will increase the photon count in each pixel. Typically, the scan rate is set to generate approximately a count of 1000 photons for pixels having fluorescently-marked targets.

At step 202, the system initializes the x-y-z translation table by locating the x-y-z stages at their home position. At step 203, the system focuses the laser on the surface 231 of the substrate. At step 204, the system locates the x-y-z table at its start position. At step 205, the system begins to translate the vertical stage, thereby collecting a series of data points over a vertical line at step 206. When a line of pixels has been scanned at step 207, the x-y-z translation table moves the horizontal stage to collect data from the next line of pixels at step 208. The collected data is written to the file as the substrate is repositioned at the top of the next line. Steps 205 through 208 are repeated until data from all regions have been collected. At step 209, the system determines if there are any more scans to be performed according to the set up parameters. If there are, the system at steps 210 and 211 determines the amount of time to wait before commencing the next scan and to either repeat the process from step 203 (if refocusing of the substrate is desired) or 204. Otherwise, the scan is terminated.

Figure 3A:
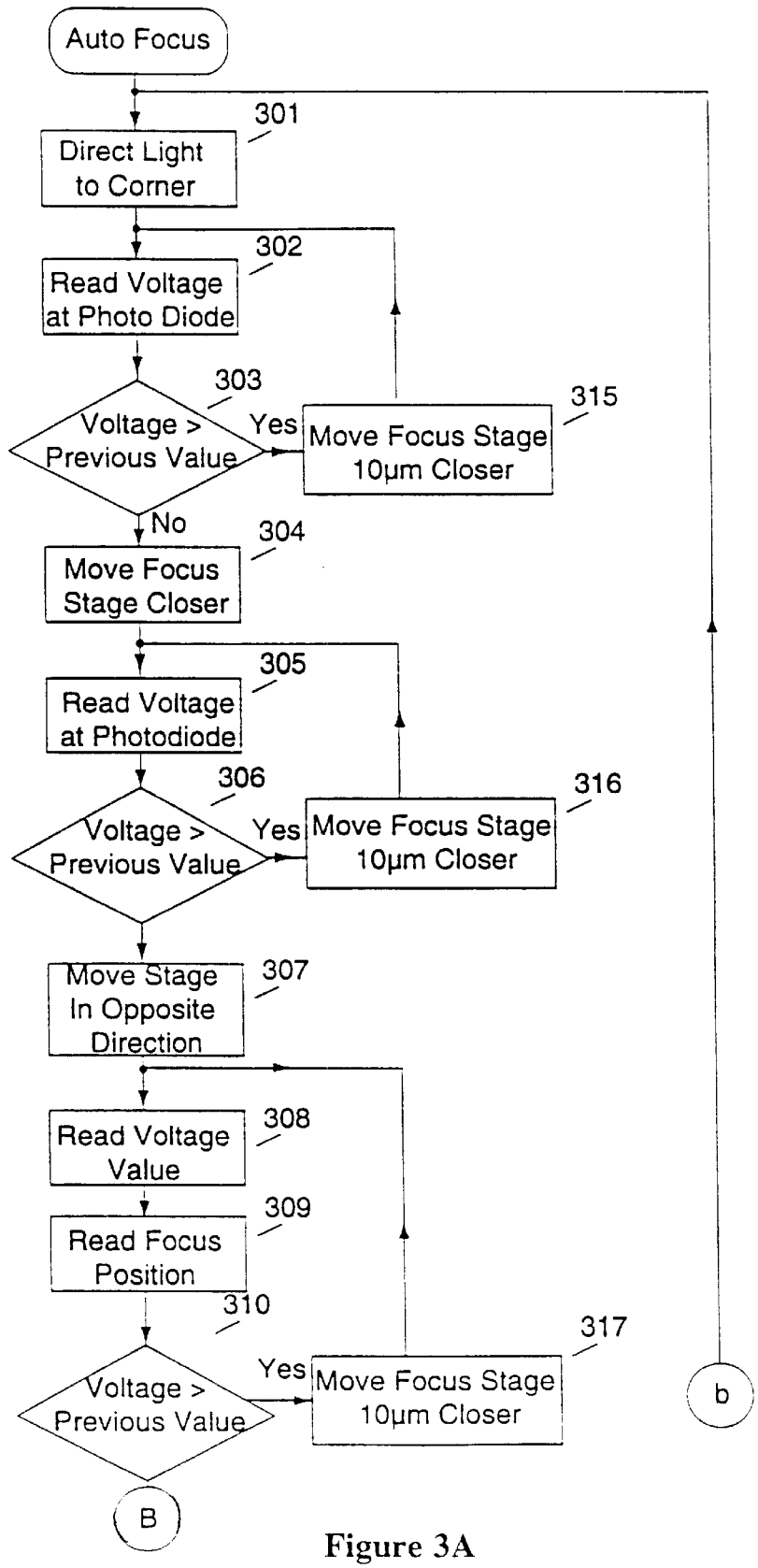
FIGS. 3a and 3b are another flow chart illustrating the focusing step of the detection system.
Figure 3B:
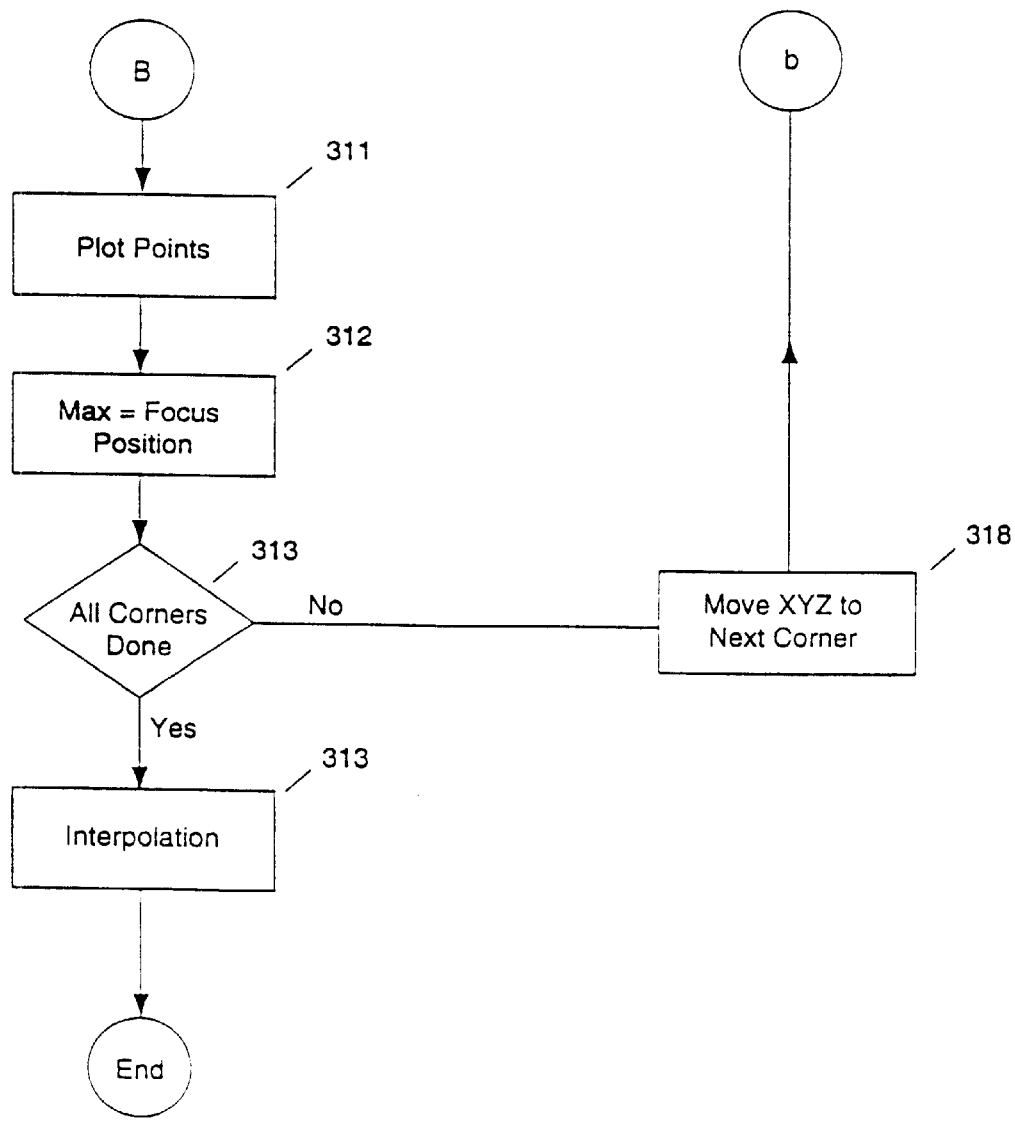

FIG. 3 illustrates the focusing step 203 in greater detail. Auto-focusing is accomplished by the system in three phases. In the first phase, the system focuses the laser roughly on the back surface of the substrate. At step 301, the laser is directed at one corner of the substrate. After the light contacts the surface, it is reflected back through microscope objective 140 and optical lens 130 to dichroic mirror 120. The dichroic mirror reflects the light to beam splitter 110 which guides the beam to lens 175. Lens 175 focuses the light through a pinhole 171 to photodiode 170. Pinhole 171 is a confocal pinhole, which transmits light that is reflected from the surface located at the focal plane and blocks light that is reflected or scattered from other surfaces. At step 302, photo-diode 170 generates a voltage corresponding to the intensity of the reflected light. The flow cell is then moved about 10 microns closer to the microscope objective at step 315, and the process from step 302 is repeated. The loop commencing at step 302 is repeated until the voltage generated by the photodiode has peaked (i.e., the present voltage value is less than the previous voltage value), at which time, the laser is roughly focused on the backside of the substrate. Since 10 μm steps are taken, the light is focused slightly inside the substrate.

At step 304, the system continues with the next focusing phase by moving the flow cell closer to the microscope objective. In a preferred embodiment, the distance over which the flow cell is moved is about equal to half the thickness of the substrate. The default distance is 350 mm (½ the thickness of a typical substrate used) or a distance entered by the user representing half the thickness of the substrate used. Again, at step 305, photo-diode 170 generates a voltage corresponding to the intensity of the reflected light. Preferably, the flow cell is then moved about 10 microns closer at step 316, and the process from step 305 is repeated. The loop commencing at step 305 is repeated until the voltage generated by the photodiode has peaked, at which time, the laser is roughly focused on a point beyond surface 230.

At step 307, the flow cell is moved farther from the microscope objective in steps of about 1 μm. The computer reads and stores the voltage generated by the photodiode at step 308. At step 309, the encoder indicating the position of the focus stage is read and the resulting data is stored. The encoder determines the location of the focus stage to within about 1 micron. At step 310, the system determines if the present voltage value is greater then the previous value. If it is, the flow cell is then moved about 1 micron farther at step 317. Due to the presence of noise, the process from step 308 is repeated even after the voltage value has peaked. Specifically, the process is continues until the voltage generated by the photodiode 104 is less than the peak voltage minus twice the typical peak-to-peak photodiode voltage noise. At step 311, the data points are fitted into a parabola where x=encoder position and y=voltage corresponding to the position. Fitting the data points to a parabola gives a more accurate method of focusing than by merely taking the highest point due to the presence of noise in the data. At step 312, the system determines the focus position on surface 230 which corresponds to the maximum of the parabola.

At step 313, the system-determines whether all four corners have been focused. If they have been, then the process proceeds to step 314. Otherwise, the system, at step 318 moves the x-y-z translation stage for directing the light at the next corner and returns to step 301. The focussing process beginning at step 301 is repeated until the all four corners of the substrate has been focused.

At step 314, the system assumes that the substrate is planar. Thus, the focus position of other pixels are obtained by interpolating the values collected from the focusing process. In this manner, auto-focusing for each pixel of the substrate is achieved.

By using the focusing method disclosed herein, the laser is focused on surface 230 of the substrate, which is significantly less reflective than the backside of the substrate. Generally, it is difficult to focus on a weakly reflective surface in the vicinity of a strongly reflective surface. However, this problem is solved by the present invention and thus, more accurate reading of the fluorescently marked targets is achieved.

Figure 4A:
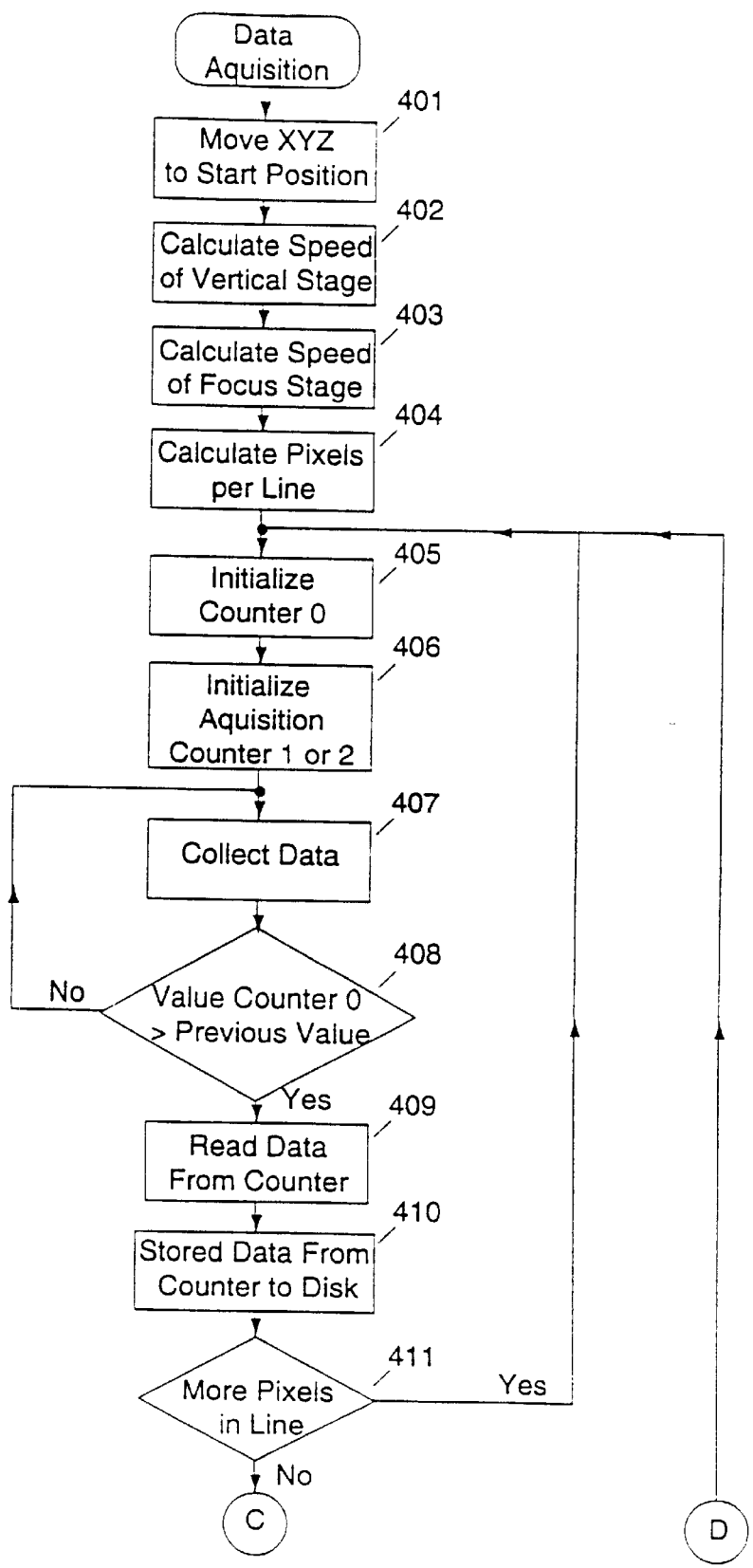
FIGS. 4a and 4b are another flow chart illustrating the data acquisition step of the detection system.

FIG. 4a illustrates the data acquisition process beginning at step 205 in greater detail. In a specific embodiment, data are collected by repeatedly scanning the substrate in vertical lines until the sample is completely scanned. However, other techniques such as repeatedly scanning the substrate in horizontal lines, bidirectional scanning (acquiring data in both directions) or others may be employed.

At step 401, the x-y-z translation table is initialized at the start position. At step 402, the system calculates the constant speed at which the vertical stage is to be moved. The speed of the vertical stage is determined from the scan speed information entered by the user. Typically the scan speed is about 10 to 30 mm/sec or a speed at which a photon count of about 1000 photons will be generated for pixels having complementary probes. At step 403, the system calculates the constant speed at which the focusing stage is to be moved in order to maintain the substrate surface 230 in focus. This speed is derived from the data obtained during the focusing phase.

At step 404, the system calculates the number of pixels per line by dividing the length of the scan line by the pixel size. At step 405, the system initializes counter 0 on the data acquisition board with a value such that a square wave having a period that is equal to twice the data acquisition time per pixel is generated. The period is calculated by dividing the pixel size information entered by the user at step 209 by the speed of the vertical stage derived from step 402. Counter 0 counts down until it reaches zero, at which time, a square wave transition has occurred, i.e., value of the square wave goes from low to high or high to low. Simultaneously, counter 0 is re-initialized with its initial value.

In a preferred embodiment, counter 1 on the data acquisition board is configured to store the photon counts from the even pixels while counter 2 is configured to store counts from the odd pixels, but other configurations may be employed. At step 406, counter 2 is initialized to zero by the rising edge of the first period of the square wave. Thereafter, counter 2 is enabled and begins to collect data at step 407.

The system, at step 408, polls counter 0 and compares the present value of counter 0 with its previous value. If the present value is less than the previous value, then counter 2 continues to accumulate photon counts. On the other hand, if the present value in counter 0 is greater than its previous value, a square wave transition has occurred. The falling edge of the square wave disables counter 2 from counting, thus, completing the scan of the first pixel. Simultaneously, counter 1 is initialized because its gate input is coupled to the inverted output of counter 0. The operation of counter 1 will be described in more detail during the discussion on the second pass of the loop beginning at step 406.

While counter 2 is disabled, the photon count stored in counter 2 is read at step 409. At step 410, the data is written and stored in memory, for example, in the form of a data structure, an array, a table or other listing means. In the alternative, the data may also be written to a data file. At step 411, the system determines if there are more pixels in the line to scan. If there are, process repeats the steps beginning at 406. Otherwise, the system proceeds to step 412.

On the second pass of the loop beginning at step 405, the inverted falling edge (rising edge) of the square wave initializes and enables counter 1 to collect data at steps 406 and 407 respectively. At step 408, the inverted rising edge (falling edge) of the square wave disables counter 1 and data therein is read at step 409 and written to the computer at step 410.

Figure 4B:
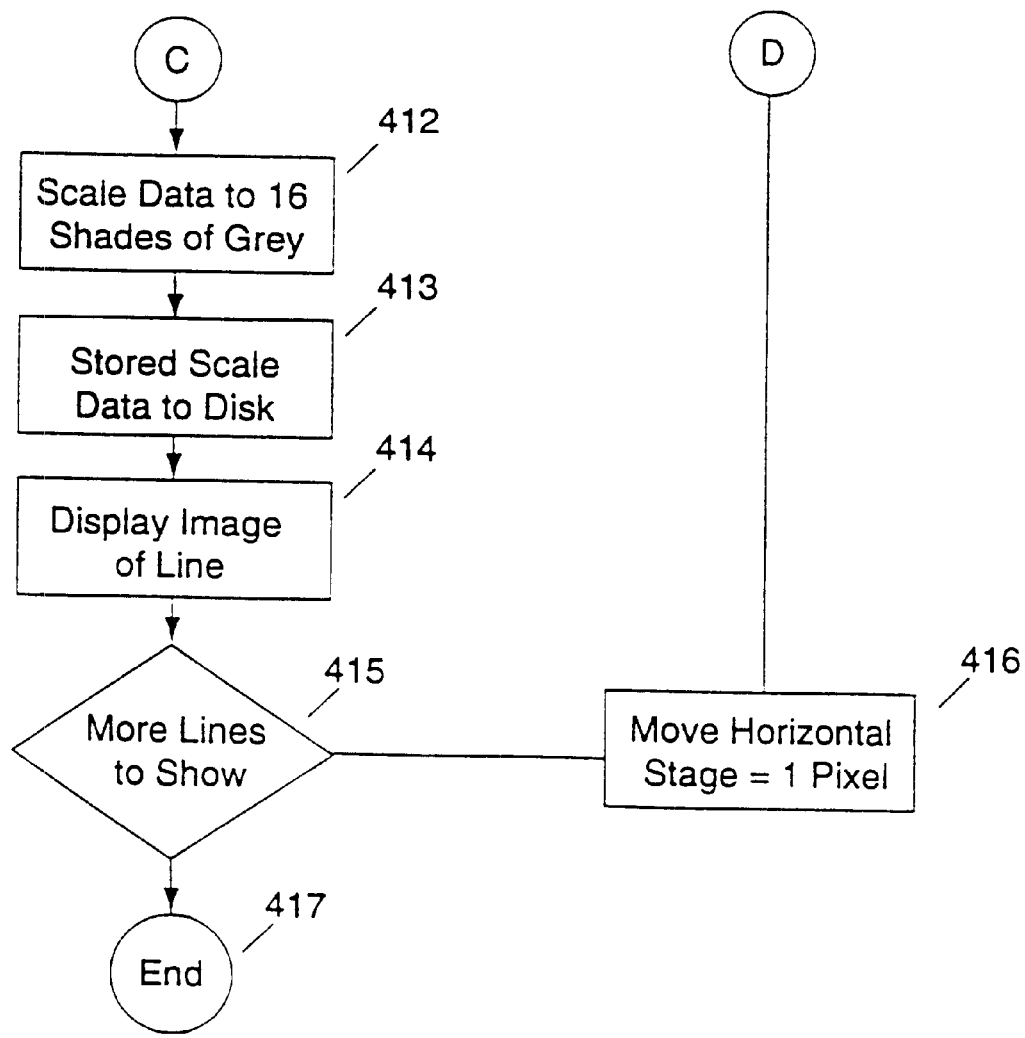
Figure 4C:
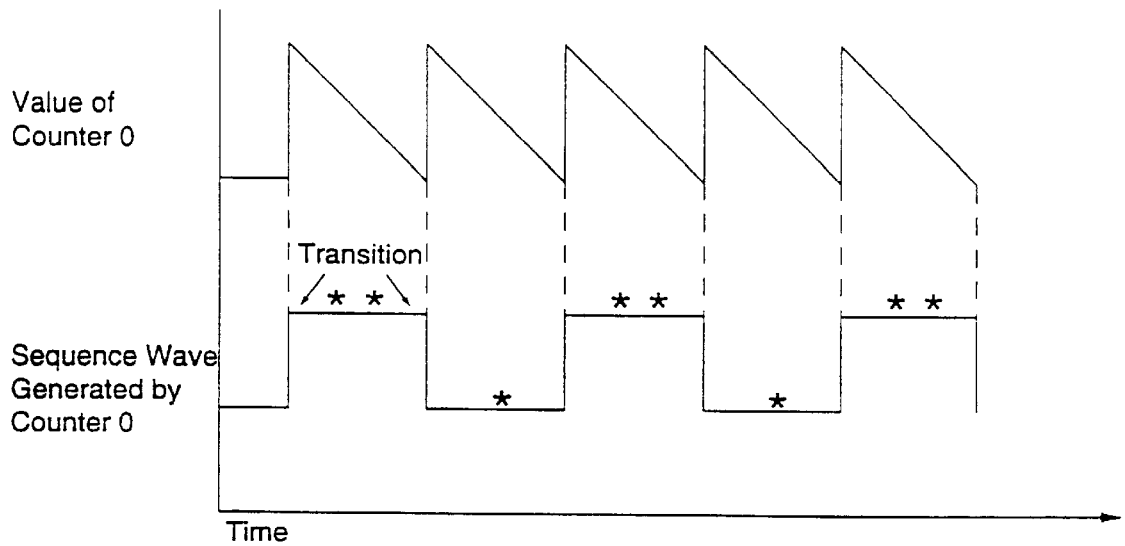
FIG. 4c shows the relationship among the counters in the data acquisition board versus time.

In the specific embodiment, the counters are preferably configured to collect and store data alternately, i.e., when counter 1 collects data, counter 2 stores data. FIG. 4b illustrates the relationship among the count value in counter 0, the square wave, counter 1 and counter 2 versus time.

At step 411, the system determines if there are more pixels left to scan. The loop from step 405 through step 411 is repeated until all pixels in the line have been scanned. After each line has been scanned, the system at step 412 calculates a gray scale for imaging. In a preferred embodiment, the gray scale contains 16 gray levels, but a scale of 64, 256 or other gray levels may be used. In alternative embodiments, a color scale may be used instead of a gray scale. Preferably, the middle of the scale corresponds to the average count value detected during the scan. Thereafter, the raw data points are stored in a data file at step 413. At step 414, the scaled data representing an image of the scanned substrate regions may be displayed on a screen or video display mean in varying shades of gray or colors. Each shade or color corresponds to the intensity level of fluorescence at the respective regions.

While the image of the previous scanned line is being displayed, the system determines if there are any more lines to scan at step 415. If so, the horizontal stage is translated in preparation for scanning the next line at step 416. The distance over which the horizontal stage is moved is equal to about 1 pixel. Simultaneously, the vertical stage is moved to the top of the next scan line. Thereafter, the system repeats the process starting at step 405 for the next scan line. The loop from step 405 to step 415 is repeated until scanning of the substrate is completed. In this manner, the system simultaneously displays and collects data. Upon completion, the system creates a data file wherein the data represents an array of photon counts as a function of substrate position.

By counting the number of photons generated in a given area in response to the excitation light, it is possible to determine where fluorescently marked molecules are located on the substrate. Consequently, it is possible to determine which of the probes within a matrix of probes is complementary to a fluorescently marked target.

According to preferred embodiments, the intensity and duration of the light applied to the substrate is controlled by the computer according to the set up parameters entered at step 201. By varying the laser power and scan stage rate, the signal-to-noise ratio may be improved by maximizing fluorescence emissions. As a result, the present invention can detect the presence or absence of a target on a probe as well as determine the relative binding affinity of targets to a variety of sequences.

In practice it is found that a target will bind to several peptide sequences in an array, but will bind much more strongly to some sequences than others. Strong binding affinity will be evidenced herein by a strong fluorescence signal since many target molecules will bind to that probe. Conversely, a weak binding affinity will be evidenced by a weak fluorescence signal due to the relatively small number of target molecules which bind in a particular probe. As such, it becomes possible to determine relative binding avidity (or affinity in the case of univalent interactions) of a probe herein as indicated by the intensity of a fluorescent signal in a region containing that probe.

Semiquantitative data on affinities may also be obtained by varying set up conditions and concentration of the targets in the reagent. This may be done by comparing the results to those of known probe/target pairs.

While the detection apparatus has been illustrated primarily herein with regard to the detection of marked targets, the invention will find application in other areas. For example, the detection apparatus disclosed herein could be used in the fields of catalysis, DNA or protein gel scanning, and the like.

IV. Data Analysis System to Determine Relative Binding Strength of Targets

Before the data file representing an array of photon counts as a function of position is analyzed to determine the relative binding affinity of targets, the data file is preferably converted to an image file wherein the data is indicative of fluorescence intensity level as a function of substrate position.

Figure 5:
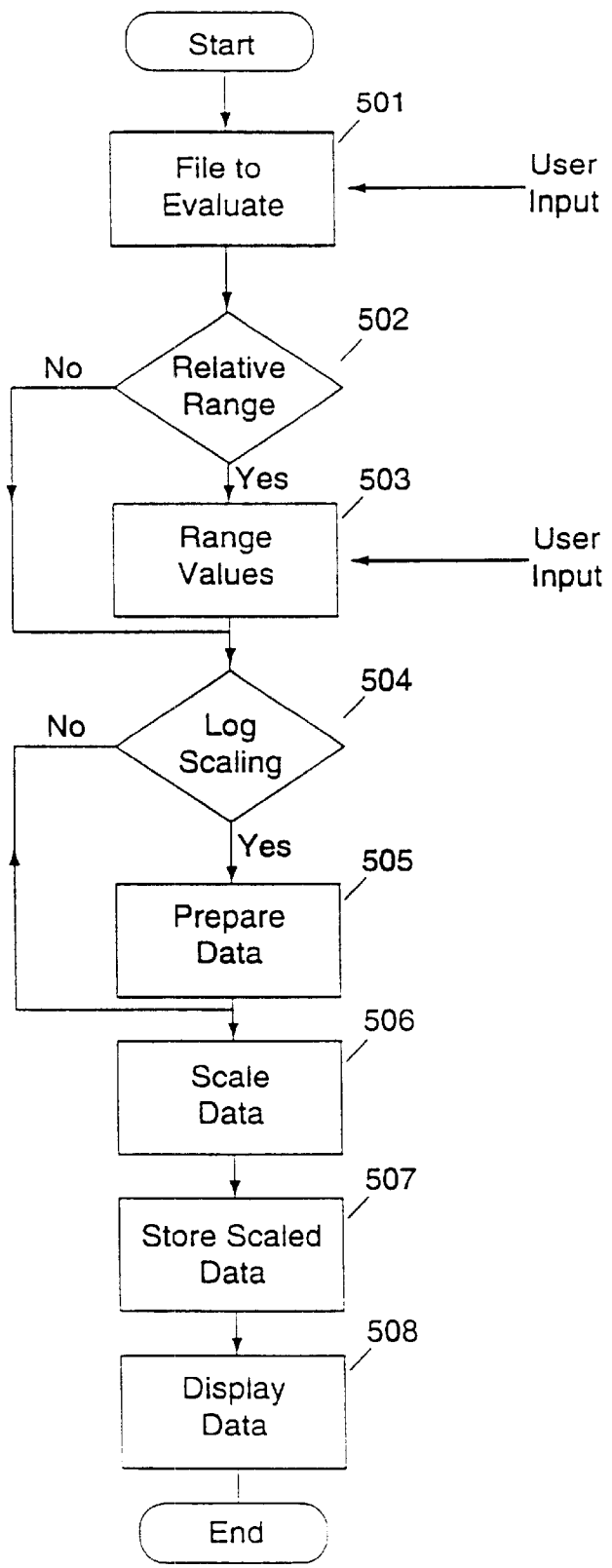
FIG. 5 is another flow chart illustrating the method of converting data representing photon counts as a function of position to data representing fluorescence intensity level as a function of position.

FIG. 5 illustrates the process for converting or scaling the data from photon counts to fluorescence intensity level in greater detail. The conversion procedure is started by prompting the operator for the name of data file of interest. At step 501, the system retrieves the specified data file for analysis.

At step 502, the user directs the system to scale the data either in relative range or absolute range mode. In the absolute range mode, the data is scaled by using the set of values between the minimum and maximum number of photons. If absolute range mode is chosen, the system proceeds to step 504 which will later be described.

On the other hand, if relative range mode is chosen, the system proceeds to step 503. Scaling the data in relative range is advantageous. Particularly, relative range mode minimizes the effect of aberrations resulting from dirt or other imperfections on the substrate by ignoring a certain percentage of data points at the intensity extremes. From experience, this range is typically from about 1% of the lowest values and 0.03% of the highest values. At step 503, the user enters the range values or in the alternative, the system may provide for default values. For example, if the user enters 0.03% and 1% as the relative range values and there are 100,000 pixels in the image, the brightest 30 pixels (0.003×100,000) and dimmest 1000 (0.1×100,000) pixels are clipped (clamped to its next highest or lowest value respectively).

At step 504, the system determines if the dynamic range (i.e., the ratio of the count in the brightest pixel and the dimmest pixel) of the image is high. If the ratio is high, the system prepares the data for logarithmic scaling at step 505. Otherwise, the system proceeds to step 506 where the data will be scaled linearly. In alternative embodiments, the system may prepare the data for square root scaling instead of logarithmic scaling. In this manner, lost of valid data at the low intensities having low photon counts are avoided, thereby, increasing the resolution at these intensities.

At step 506, the system obtains the minimum and maximum photon counts from the data. The range between these two count values is used to scale the data into digitized units. Preferably, the digitized units have a range from 0 to 255, each one representing a gray level or a color. Alternatively, other ranges such as from 0 to 63 may be used. Generally, the average photon count value is placed in the middle of scale.

Upon completion of the conversion process, an image file representing fluorescence intensity is created and stored in memory at step 507. At step 508, the system may optionally display the image file. The intensity level of the displayed image varies from region to region according to the binding affinity of the targets to the polymer sequence therein. The brightest signals typically represent the greatest binding affinity while signals of lesser intensity represent lesser degrees of binding affinity.

As described, data are collected over regions substantially smaller than the area in which a given polymer or feature is synthesized. For example, the length of a pixel is generally ¼ to ¹⁄₁₀ the length of a feature (or the area of a pixel is ¹⁄₁₆ to ¹⁄₁₀₀ the area of a feature). Hence, within any given feature, a large number of fluorescence data points or pixels are collected.

A plot of the number of pixels versus the fluorescence intensity for a scan of a substrate synthesized with probes when it has been exposed to, for example, a labeled antibody will typically take the form of a bell curve. However, spurious data are observed, particularly at higher intensities. Since it is preferable to used an average of the fluorescence intensity over a given synthesis region in determining the relative binding affinity, these spurious data points will tend to undesirably skew the data.

Figure 6A:
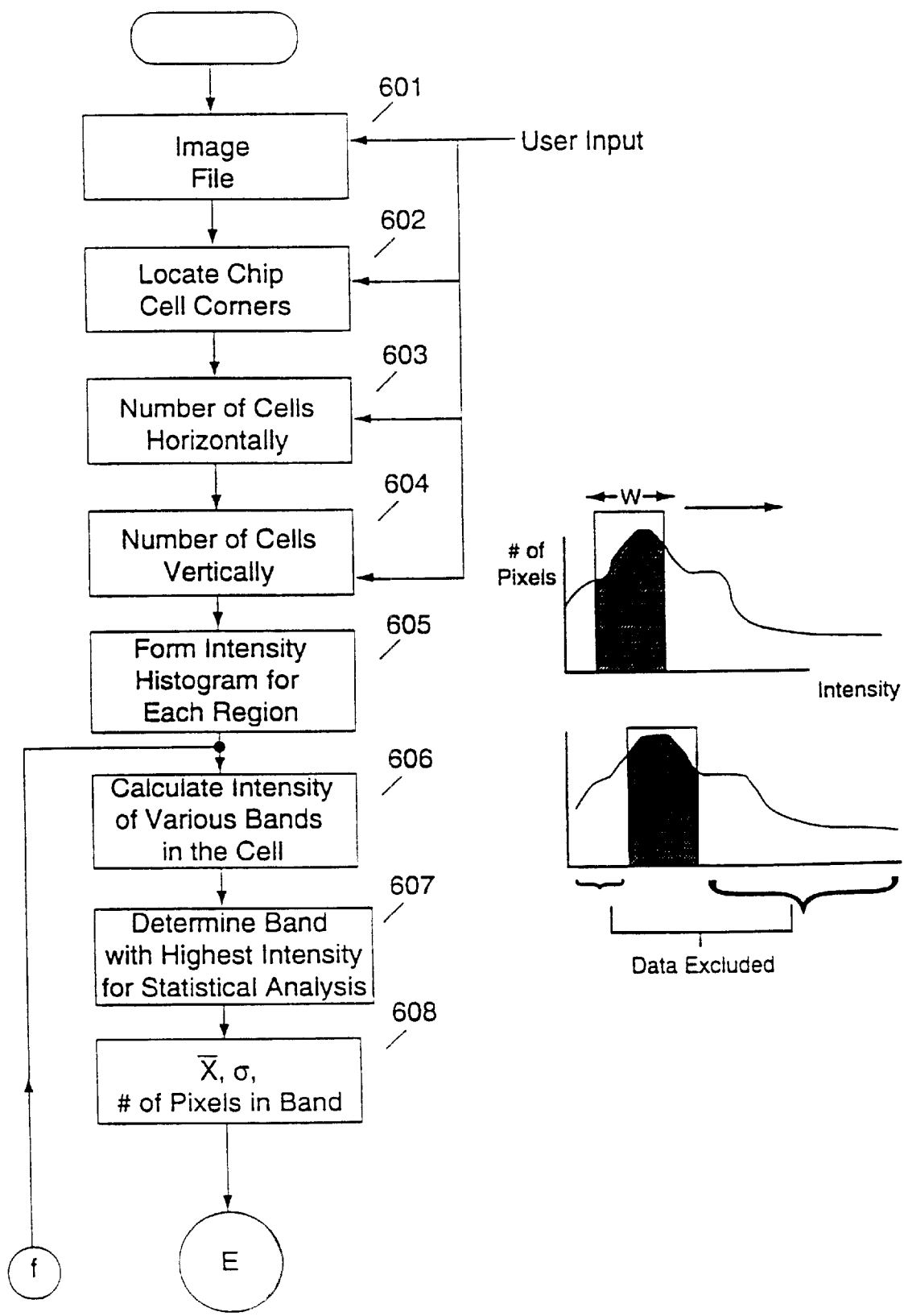
FIGS. 6a and 6b are another flow chart illustrating the data analysis step.
Figure 6B:
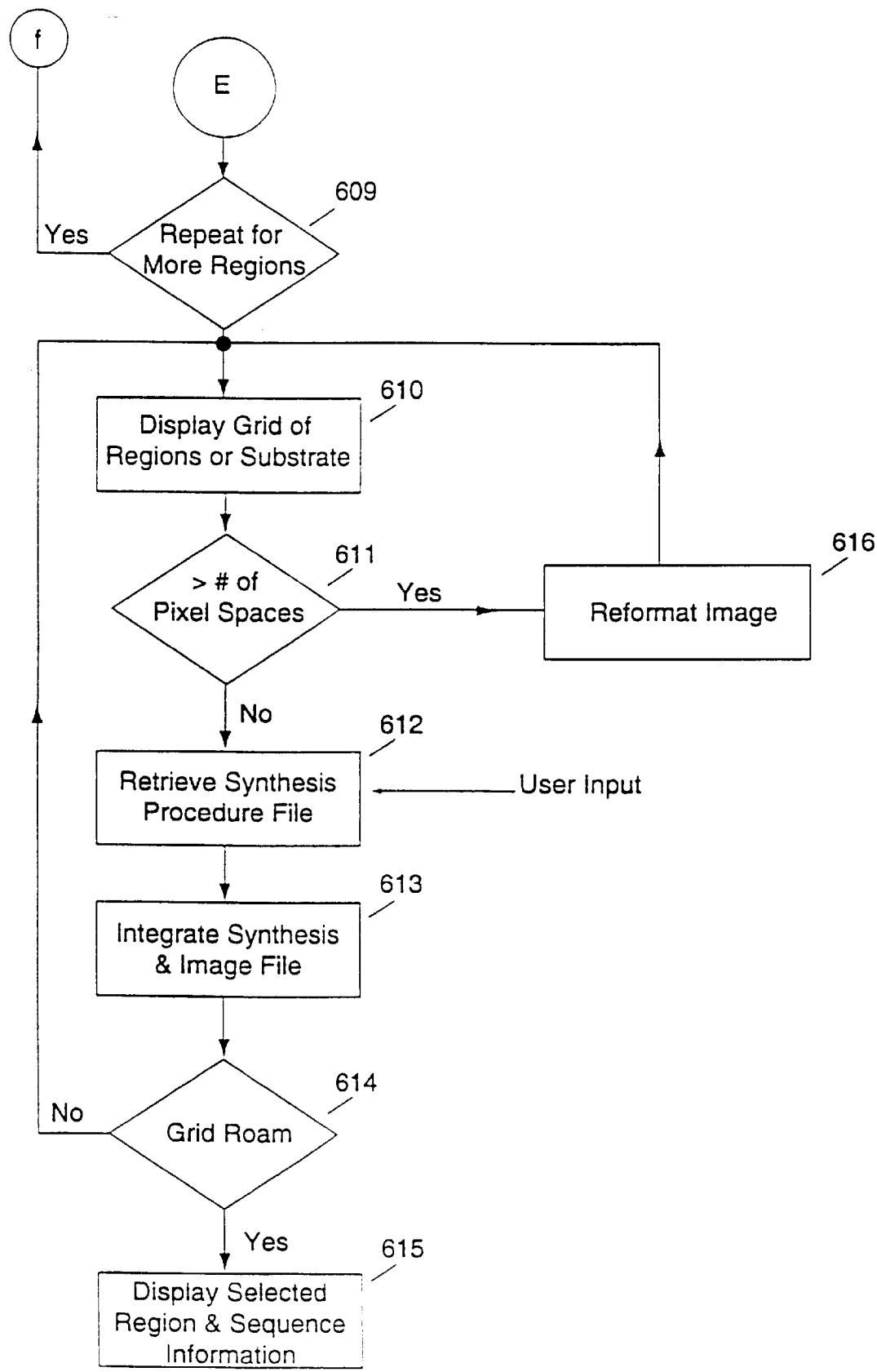

FIG. 6 illustrates one embodiment of the of a system which provides for the removal of these undesirable spurious data points as well as the determination of the relative binding efficiency of the sample from an average of the remaining data points.

Referring to FIG. 6, the system is initialized by requesting the user to enter the name of a image file of interest. At step 601, the system retrieves the image file and prompts the user to enter the four corners of the image at step 602. Next, at steps 603 and 604, the system prompts the user for the number of cells located horizontally and vertically on the substrate. From the information entered by the user and the image file, the system creates a computer representation of a histogram for each cell at step 605. The histogram (at least in the form of a computer file) plots the number of pixels versus intensity.

At step 606, the main data analysis loop is performed for each synthesis site. Analyzing the histogram for the respective synthesis site, the system calculates the total intensity level and number of pixels for the bandwidth centered around varying intensity levels. For example, as shown in the plots to the right of step 606, the system calculates the number of pixels in the bandwidth using boxcar averaging technique. This process is then repeated until the entire range of intensities have been scanned. At step 607, the system determines which band has the highest total number of pixels. The data from this band is used to derive statistical data for each synthesis site. The statistical data include the peak value, mean intensity and standard deviation of intensity level. Thus, data that are beyond this band are excluded from the statistical analysis. Assuming the bandwidth is selected to be reasonably small, this procedure will have the effect of eliminating spurious data located at both the higher and lower intensity levels. This loop is repeated until all the cells have been processed.

At step 610, an image in the form of a grid representing the substrate is displayed. Each block in the grid represents a region synthesized with a polymer sequence. The image intensity of each region will vary according to the binding affinity between the polymer sequence and targets therein. Statistical data, such as the peak and average intensity corresponding to each region are also displayed.

To improve imaging, pixels located at transitions between synthesis regions are ignored. The image, in some instances, requires only one pixel space between the cells when the transition of the intensity between the synthesis regions is sharp and distinct. However, if the transition is fuzzy or smeared, the user, at step 611, can select a greater number of pixel spaces between the cells to increase image resolution. If the user enters a value indicating a greater number of pixel spaces is desired, the system at step 616 reformats the image accordingly.

At step 612, the system retrieves the file created during the synthesis process of the substrate being analyzed. The synthesis file contains sequence information as a function of location. The system integrates the synthesis file with the image file and sorts the data therein. Through this process, the molecular sequence of complementary probes and the intensity as a function of location is available.

Further, the user, at step 614, may analyze a specific synthesis region within the grid. If instructed, the system will display the corresponding substrate position, number of photons, number of pixels and the molecular sequence at that synthesis site. The data analysis software also provides the user with many functions which are common to image processing, such as magnification and image enhancement.

V. Conclusion

The present invention provides greatly improved methods and apparatus for detection of intensity of fluorescence on a substrate. It is to be understood that the above description is intended to be illustrative and not restrictive. Many embodiments will be apparent to those skill in the art upon reviewing the above description. Although the detection apparatus has been illustrated primarily herein with regard to the detection of marked targets, it will readily find application in other areas. For example, the detection apparatus disclosed herein could be used in the fields of catalysis, DNA or protein gel scanning, and the like. The scope of the invention should, therefore, be determined not with the reference to the above description, but should instead be determined with reference to the appended claims, along with the full scope of equivalents to which such claims are entitled.

What is claimed is:

1. An apparatus comprising:
   an optical scanning system comprising a light source; an optical train for directing excitation light from said light source toward a substrate including a surface having biological polymers with fluorescently marked regions; a translation system co-operatively arranged with said optical train and coupled to said substrate; a focusing system for focusing said light onto said surface including said biological polymers with fluorescently marked regions; and a confocal detector for detecting said fluorescent light from said fluorescently marked regions in response to said excitation light; and
   a flow cell comprising a mounting surface and a cavity, wherein said mounting surface is constructed to receive said substrate in a sealed relationship with respect to said cavity, whereby said surface having biological polymers is in fluid communication with said cavity.

2. The apparatus as recited in claim 1, wherein said focusing system comprises means for determining a focal plane of the light passing through the optical train and means for providing data for locating said surface of said substrate at said focal plane.

3. The apparatus of claim 1, further comprising:
   a photodiode for detecting light reflected from said substrate;
   a focusing lens for focusing said reflected light from said substrate, from said optical train at said photodiode; and
   a drive connected to said substrate.

4. The apparatus of claim 1, wherein the detector comprises:
   a photomultiplier tube; and
   a lens for focusing said fluoresced light separated by said optical train, at said photomultiplier tube.

5. The apparatus as recited in claim 1, wherein said flow cell includes a temperature sensor disposed adjacent to or within the cavity of said flow cell and a control system for controlling temperature in said cavity of said flow cell.

6. The apparatus of claim 5, wherein the flow cell defines one or more channels for directing heat exchanging fluid therethrough to control temperature in said cavity.

7. The apparatus of claim 1, wherein said substrate is light transparent.

8. The apparatus of claim 1, wherein said surface has said biological polymers immobilized thereon prior to mounting said substrate to said flow cell.

9. The apparatus of claim 1, wherein said translation system includes an x-y-z translation table.

10. The apparatus of claim 1, wherein said translation system includes an x-y-z translation table, and wherein said flow cell is attachable to said translation table.

11. The apparatus of claim 10, wherein said flow cell is attached to said translation table, and wherein said attached flow cell is constructed to receive fluid for hybridization of said biological polymers to targets thereby creating said fluorescently marked regions.

12. The apparatus of claim 1, wherein said scanning system is constructed to store intensities of said fluorescent light emitted from said fluorescently marked regions over at least a portion of said surface said having biological polymers in order to create a corresponding image.

13. An apparatus comprising:
   an optical scanning system comprising a light source; an optical train for directing excitation light from said light source toward a substrate including a surface having biological polymers with fluorescently marked regions; a translation system co-operatively arranged with said optical train and coupled to said substrate; a focusing system for focusing said light onto said surface including said biological polymers with fluorescently marked regions; and a confocal detector for detecting said fluorescent light from said fluorescently marked regions in response to said excitation light; and
   a flow cell comprising a mounting surface and a cavity, wherein said mounting surface is constructed to receive said substrate in a sealed relationship with respect to said cavity, whereby said surface having biological polymers is in fluid communication with said cavity.

14. The apparatus of claim 13, wherein said confocal detector includes a confocal, pinhole and an associated lens.

15. The apparatus of claim 13, wherein said substrate is light transparent.

16. The apparatus of claim 13, wherein said substrate is removably attachable to said flow cell.

17. The apparatus of claim 13, wherein said surface has said biological polymers immobilized thereon prior to mounting said substrate to said flow cell.

18. The apparatus of claim 13, wherein said translation system includes an x-y-z translation table.

19. The apparatus of claim 13, wherein said translation system includes an x-y-z translation table, and wherein said flow cell is attachable to said translation table.

20. The apparatus of claim 19, wherein said flow cell is attached to said translation table, and wherein said attached flow cell is constructed to receive fluid for hybridization of said biological polymers to targets thereby creating said fluorescently marked regions.

21. The apparatus of claim 13, wherein the detector comprises a photomultiplier tube; and a lens for focusing said fluoresced light, separated by said optical train, to said photomultiplier tube.

22. The apparatus of claim 13, wherein said scanning system is constructed to store intensities of said fluorescent light emitted from said fluorescently marked regions over at least a portion of said surface having biological polymers in order to create a corresponding image.

* * * * *